(12) United States Patent
Ladani

(10) Patent No.: US 8,132,466 B2
(45) Date of Patent: Mar. 13, 2012

(54) MECHANICAL PROPERTIES TESTING DEVICE AND METHOD

(75) Inventor: Leila Ladani, Logan, UT (US)

(73) Assignee: Utah State University, North Logan, UT (US)

(*) Notice: Subject to any disclaimer, the term of this patent is extended or adjusted under 35 U.S.C. 154(b) by 405 days.

(21) Appl. No.: 12/483,115

(22) Filed: Jun. 11, 2009

(65) Prior Publication Data
US 2009/0308172 A1 Dec. 17, 2009

Related U.S. Application Data

(60) Provisional application No. 61/073,080, filed on Jun. 17, 2008.

(51) Int. Cl.
G01B 7/16 (2006.01)
G01L 1/00 (2006.01)
H01L 41/22 (2006.01)

(52) U.S. Cl. ............ 73/765; 73/774; 73/779; 29/25.35; 29/842; 29/857

(58) Field of Classification Search ............ 73/765, 73/768, 774, 779; 29/25.35; 310/328; 250/442.11; 366/127
See application file for complete search history.

(56) References Cited

U.S. PATENT DOCUMENTS

| | | | |
|---|---|---|---|
| 5,209,119 A | 5/1993 | Polla et al. | |
| 5,869,768 A | 2/1999 | Sato et al. | |
| 6,668,622 B2 * | 12/2003 | Hajduk et al. | 73/54.37 |
| 7,377,179 B2 | 5/2008 | Anderson | |
| 2008/0236255 A1 * | 10/2008 | Martinoty et al. | 73/54.38 |

OTHER PUBLICATIONS

Brown, Stuart B; Van Arsdell, William; Mulstein, Christopher L., "Materials reliability in MEMS devices," Solid State Sensors and Actuators, 1997. Transducers '97 Chicago., 1997 International Conference on , vol. 1, no., pp. 591-593 vol. 1, Jun. 16-19, 1997 doi: 10.1109/Sensor.1997.613720 URL: http://ieeexplore.ieee.org/stamp/stamp.jsp?tp=&arnumber=613720&isnumber=13397.

Fischer EE, Labossiere PE. MEMS fatigue testing to study nanoscale material response. In: Proc. of the 2002 SEM annual conf. & exp. on experimental and applied mechanics. 2002. p. 233-235.

* cited by examiner

*Primary Examiner* — Lisa Caputo
*Assistant Examiner* — Roger Hernandez-Prewitt

(57) ABSTRACT

A mechanical property testing device and method for reliably measuring strain and fatigue characteristics of material specimens is described. An input electrical signal is applied to create an electric field around a first piezoelectric member. The resultant deformation of the first piezoelectric member transfers a force to the specimen being tested which transfers a force to a second piezoelectric member causing deformation. The deformation of the second piezoelectric member generates an output electrical field which is measured. The stress state of the specimen is calculated from fundamental material constants and the measured output electrical field.

24 Claims, 6 Drawing Sheets

MECHANICAL PROPERTIES TESTING DEVICE AND METHOD

RELATED APPLICATIONS

This application claims the benefit of U.S. Provisional Patent Application Ser. No. 61/073,080 filed on Jun. 17, 2008.

FIELD OF THE INVENTION

The present invention relates to a device and method for testing materials, and more particularly, to a piezoelectric device for measuring the mechanical properties of materials.

BACKGROUND OF THE INVENTION

Measurement of mechanical properties of microscale samples of material, such as thin films, is very difficult due to the small size of the material. The material properties of small structures and thin films cannot be easily related to the properties of bulk samples because of several reasons. Samples used for bulk mechanical testing generally have dimensions significantly greater than microstructural features, whereas in thin films, the geometrical and microstructural dimensions are on the same order of magnitude. Therefore, assumption of homogeneity and isotropy is not valid when obtaining the mechanical properties. Furthermore, different manufacturing techniques are used in fabricating small specimens and thin films resulting in different microstructure than bulk materials. In addition, because of comparable size of the structural dimensions and microstructural and defect dimensions, inelastic deformation mechanisms are far different from bulk specimens.

Testing materials at scales smaller than a millimeter is a challenge due to limiting factors such as specimen gripping techniques, the application of small forces, and the ability to measure small strain values. Therefore, conventional instruments cannot be used to test these properties. A challenge for creating new microscale testing systems is the design of reliable loading and data capture methods. Regular strain gages are not applicable due to their large size, and strain measurement techniques such as capacitive gages and digital image correlation are either expensive, hard to use, or not accurate enough. In addition, digital imaging correlation is a slow and labor intensive process that is not practical for long term fatigue tests.

The Measurement of mechanical properties of micro-scale samples is particularly challenging in fatigue testing of materials since load and displacement are both needed to be monitored for many cycles. The present invention is a device and method that addresses the need for applying load and measuring deformation at small scale as well as long term fatigue testing and reliable strain measurements on micro-scale samples.

SUMMARY OF THE INVENTION

The disclosed device is designed to perform tension, or compression, or tension-compression cyclic testing of microscale specimens and thin stand alone films of materials. The objective is to facilitate measuring both strain and stress in the materials only by monitoring input and output electrical signals. The device consists of two piezoelectric members that are fabricated on both sides of the specimen in a frame. The input electrical signal induces some amount of deformation in the first piezoelectric material resulting in a force that is transferred to the material being tested. The test material deforms and at the same time transfers a force to the second piezoelectric member causing some amount of deformation in the second piezoelectric member which subsequently induces output signals that are measured. Knowing the fundamental material constants of the piezoelectric material, stresses and strains are calculated from the input and output electrical signals.

Although the device and method were developed for micro-scale size specimens, it is clear to those skilled in the art that the device and method can be used to measure the material properties in macro-scale specimens. The principle is valid for any scale. In addition, this apparatus can be used to monitor the change in mechanical properties of many types of materials. The change in properties could be a secondary effect of a primary substance or process. For example, certain polymers change their stiffness when exposed to water or certain chemicals. This stiffness change can be measured and monitored using the disclosed apparatus and method. Therefore, chemical and biological sensors may be built based on the same principle.

BRIEF DESCRIPTION OF THE DRAWINGS

Understanding that drawings depict only certain preferred embodiments of the invention and are therefore not to be considered limiting of its scope, the preferred embodiments will be described and explained with additional specificity and detail through the use of the accompanying drawings.

DETAILED DESCRIPTION OF THE PREFERRED EMBODIMENTS

Figure 1:
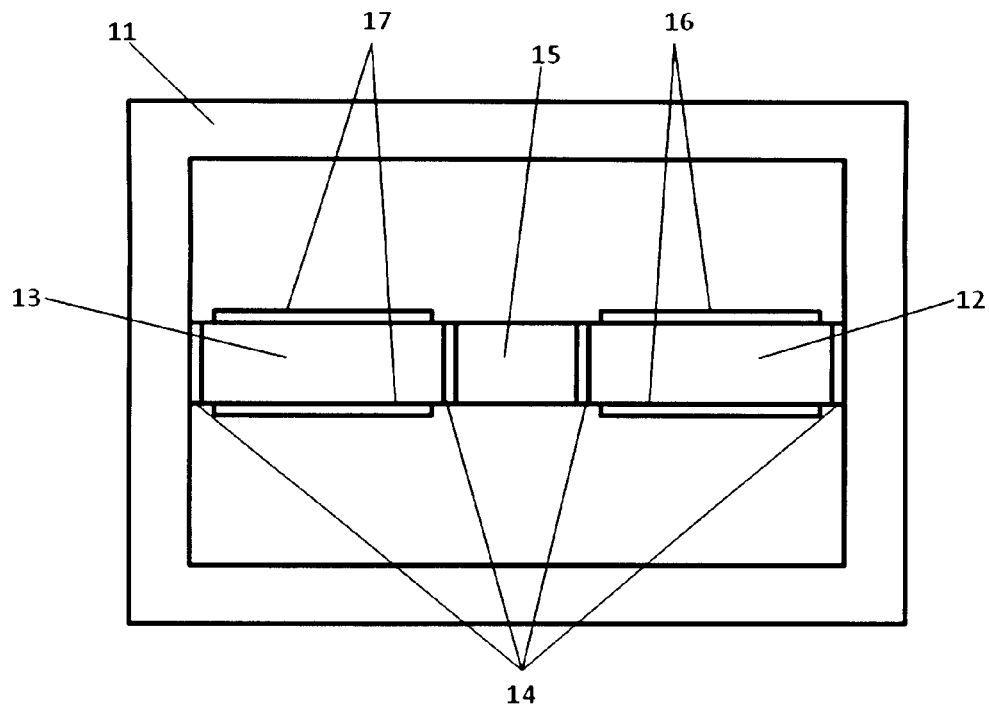
FIG. 1 is a drawing of the mechanical properties testing device.

In the following description, numerous specific details are provided for a thorough understanding of specific preferred embodiments. However, those skilled in the art will recognize that embodiments can be practiced without one or more of the specific details, or with other methods, components, materials, etc. In some cases, well-known structures, materials, or operations are not shown or described in detail in order to avoid obscuring aspects of the preferred embodiments. Furthermore, the described features, structures, or characteristics may be combined in any suitable manner in a variety of alternative embodiments. Thus, the following more detailed description of the embodiments of the present invention, as represented in the drawings, is not intended to limit the scope of the invention, but is merely representative of the various embodiments of the invention.

One embodiment of the mechanical property testing device is shown in FIG. 1. A frame 11 provides a rigid structure that does not deform under the applied testing loads. The first piezoelectric member 12, with a layer of nonconductive material 14 on each end, is positioned against one side of the frame 11. The second piezoelectric member 13, with a layer of nonconductive material 14 on each end, is positioned against the opposite side of the frame 11 such that the axis of the first piezoelectric member 12 and the second piezoelectric member 13 are colinear. The test specimen 15 is located between the first piezoelectric member 12 and the second piezoelectric member 13 such that the test specimen 15 is in contact with a layer of nonconductive material 14 on each end of both the first piezoelectric member 12 and the second piezoelectric member 13. The layers of nonconductive material 14 confine the electric fields and currents to the piezoelectric material. The nonconductive material 14 is optional if the first piezoelectric member 12 and the second piezoelectric member 13 are in contact with nonconductive materials or are nonconductive themselves.

The geometry of the first piezoelectric member 12 and the second piezoelectric member 13 can be circular rods, square rods, rectangular rods, or any other appropriate geometry. The first piezoelectric member 12 and the second piezoelectric member 13 can be selected from a variety of ceramic materials, polymers, manmade crystals, natural crystals, and other natural materials. The first piezoelectric member 12 and the second piezoelectric member 13 can be the same chemical composition but they do not necessarily have to be. A partial list of piezoelectric materials is presented in Table 1. Those skilled in the art will recognize other piezoelectric materials that can be used in the disclosed invention.

TABLE 1

| Piezoelectric Materials | | |
| --- | --- | --- |
| barium titanate | lead titanate | Lead zirconate titanate |
| potassium niobate | lithium niobate | lithium tantalite |
| sodium tungstate | quartz | polyvinylidene fluoride |

With continuing reference to FIG. 1, input conducting layers or plates 16 are located adjacent to the first piezoelectric member 12 such that when an input electrical signal is generated an electrical field is created between the input conducting plates 16. These input conducting plates 16 can be in contact with the first piezoelectric member 12 or sufficiently close to generate an electric field around the first piezoelectric member 12. The lengths of the input conducting plates 16 are slightly less than the length of the first piezoelectric member 12 such that they do not come in contact with the frame 11 or the test specimen 15.

Also shown in FIG. 1 are the output conducting layers or plates 17 which are located alongside the second piezoelectric member 13. The lengths of the output conducting plates 17 are slightly less than the lengths of the second piezoelectric member 13 such that they do not come in contact with the frame 11 or the test specimen 15. The output electrical signal detected by the output conducting plates 17 are measured by standard techniques known to those skilled in the art.

A standard test procedure begins with mounting the specimen between the first and second piezoelectric member. If the specimen is conductive, layers of non-conductive material are placed between the specimen and piezoelectric members. The specimen, piezoelectric members, and nonconductive layers are secured together by epoxy, or bonding or other known means to attach the materials together and create a co-linear structure which is secured within the frame. The input conducting plates are used to generate an electric field around the first piezoelectric member which induces a shape change in the first piezoelectric member. This shape change exerts a force on the specimen. Since the specimen is constrained against the second piezoelectric member, the applied force will cause the specimen to deform and induce a force on the second piezoelectric member. This force will be translated to deformation in the second piezoelectric member, thus producing an output electric signal that is picked up by the output conducting plates. Knowing the fundamental material constants of the piezoelectric material, stresses and strains are calculated from the input and output electrical signals. The magnitude of the applied electric field determines the applied load, or force exerted on the specimen. The electric field can be applied such that the specimen is in tension or compression or it can be cycled from one to the other, thus tension, or compression, or tension-compression cyclic testing can be performed.

Both the first piezoelectric member and the second piezoelectric member are governed by the following equation, $$S = d_1 E + s^E T \qquad 1$$

where S is the strain of the material, E is the electric field applied, T is the stress in the material. The meaning of each material constant is given in the table below.

| Symbol | Description | Unit |
| --- | --- | --- |
| T | Stress | Pa |
| S | Strain | m/m |
| E | Electric field | V/m |
| d | Piezoelectric strain constant | C/N |
| s | Elastic compliance | m²/N |

The equations are expanded for one example material for clarity. $LiNbO_3$ properties are given blow:

$$d = \begin{bmatrix} 0 & 0 & 0 & 0 & 69.2 & -20.8 \\ -20.8 & 20.8 & 0 & 69.2 & 0 & 0 \\ -0.85 & 0 & 6 & 0 & 0 & 0 \end{bmatrix} \times 10^{-12} \frac{C}{N} \qquad 2$$

$$s^E = \begin{bmatrix} 5.831 & -1.150 & -1.452 & -1.000 & 0 & 0 \\ -1.150 & 5.831 & 1.452 & 1.000 & 0 & 0 \\ -1.452 & 1.452 & 5.026 & 0 & 0 & 0 \\ -1.000 & 1.000 & 0 & 17.10 & 0 & 0 \\ 0 & 0 & 0 & 0 & 17.10 & -1.000 \\ 0 & 0 & 0 & 0 & -1.00 & 13.96 \end{bmatrix} \times 10^{-12} \frac{m^2}{N} \qquad 3$$

Figure 2:
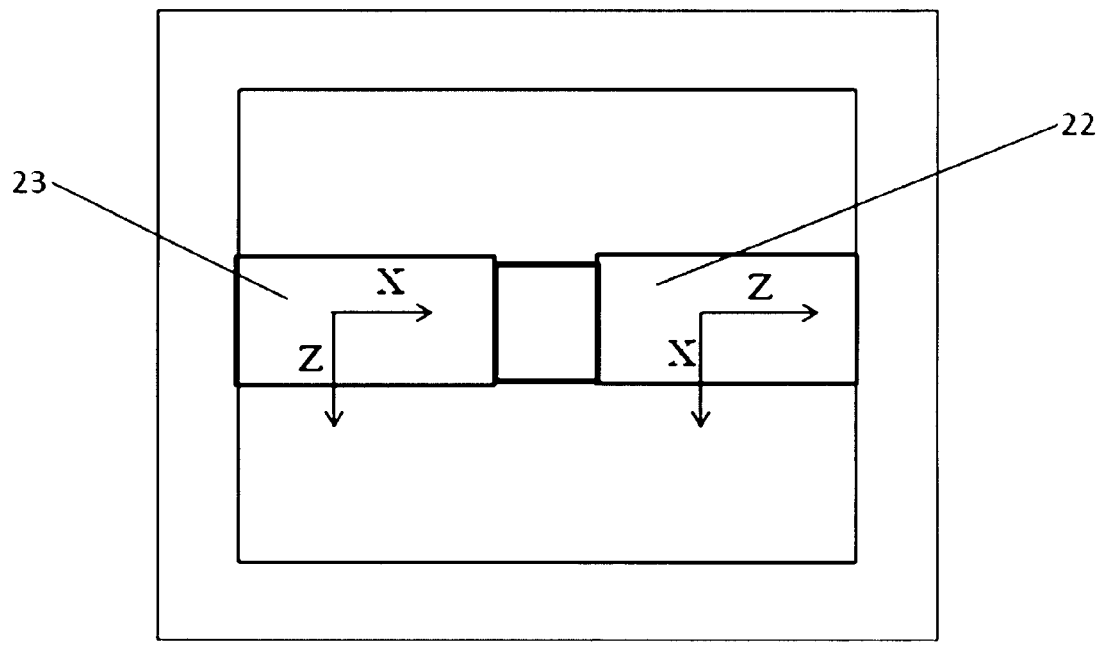
FIG. 2 is a diagram showing the crystallographic orientation of the piezoelectric membranes in one embodiment.

For the example shown in FIG. 2, where the first piezoelectric member 22 is oriented in the (001) crystal orientation (z) and the second piezoelectric member 23 is oriented in the (100) crystal orientation (x), and the electric field is applied in the z direction, the equations for the first piezoelectric member are:

$$S = \begin{bmatrix} 0 & -20.8 & -0.85 \\ 0 & 20.8 & 0 \\ 0 & 0 & 6 \\ 0 & 69.2 & 0 \\ 69.2 & 0 & 0 \\ -20.8 & 0 & 0 \end{bmatrix} \begin{bmatrix} 0 \\ 0 \\ E_3 \end{bmatrix} + \qquad 4$$

$$\begin{bmatrix} 5.831 & -1.150 & -1.452 & -1.000 & 0 & 0 \\ -1.150 & 5.831 & 1.452 & 1.000 & 0 & 0 \\ -1.452 & 1.452 & 5.026 & 0 & 0 & 0 \\ -1.000 & 1.000 & 0 & 17.10 & 0 & 0 \\ 0 & 0 & 0 & 0 & 17.10 & -1.000 \\ 0 & 0 & 0 & 0 & -1.00 & 13.96 \end{bmatrix} \begin{bmatrix} 0 \\ 0 \\ T_3 \\ 0 \\ 0 \\ 0 \end{bmatrix}$$

where E, T and S are in V/m, Pa, and μm/m respectively.

$$S = \begin{bmatrix} -0.85E_3 \\ 0 \\ 6E_3 \\ 0 \\ 0 \\ 0 \end{bmatrix} + \begin{bmatrix} -1.452T_3 \\ 1.452T_3 \\ 5.026T_3 \\ 0 \\ 0 \\ 0 \end{bmatrix} \quad 5$$

In this equation $E_3$ is the input signal and is known. The equations for the second piezoelectric member then can be written as:

$$S = \begin{bmatrix} 0 & -20.8 & -0.85 \\ 0 & 20.8 & 0 \\ 0 & 0 & 6 \\ 0 & 69.2 & 0 \\ 69.2 & 0 & 0 \\ -20.8 & 0 & 0 \end{bmatrix} \begin{bmatrix} E_1 \\ E_2 \\ E_3 \end{bmatrix} + \quad 6$$

$$\begin{bmatrix} 5.831 & -1.150 & -1.452 & -1.000 & 0 & 0 \\ -1.150 & 5.831 & 1.452 & 1.000 & 0 & 0 \\ -1.452 & 1.452 & 5.026 & 0 & 0 & 0 \\ -1.000 & 1.000 & 0 & 17.10 & 0 & 0 \\ 0 & 0 & 0 & 0 & 17.10 & -1.000 \\ 0 & 0 & 0 & 0 & -1.00 & 13.96 \end{bmatrix} \begin{bmatrix} T_1 \\ 0 \\ 0 \\ 0 \\ 0 \\ 0 \end{bmatrix}$$

In the second piezoelectric member there is only traction in the x direction. Simplifying these equations results in following equation:

$$S = \begin{bmatrix} -20.8E_2 - 0.85E_3 + 5.831T_1 \\ 20.8E_2 - 1.150T_1 \\ 6E_3 - 1.452T_1 \\ 69.2E_2 - T_1 \\ 69.2E_1 \\ -20.8E_1 \end{bmatrix} \quad 7$$

If the characteristics of the second piezoelectric member are known, then by knowing the output signals, $E_3$, the traction and strains can be calculated from equation 7. By knowing the traction which is the same and opposite direction of the traction in the first piezoelectric member, then the strain in the first piezoelectric member is known and therefore, the strain in the specimen can be calculated by deducting the strain in these two pieces.

Figure 3:
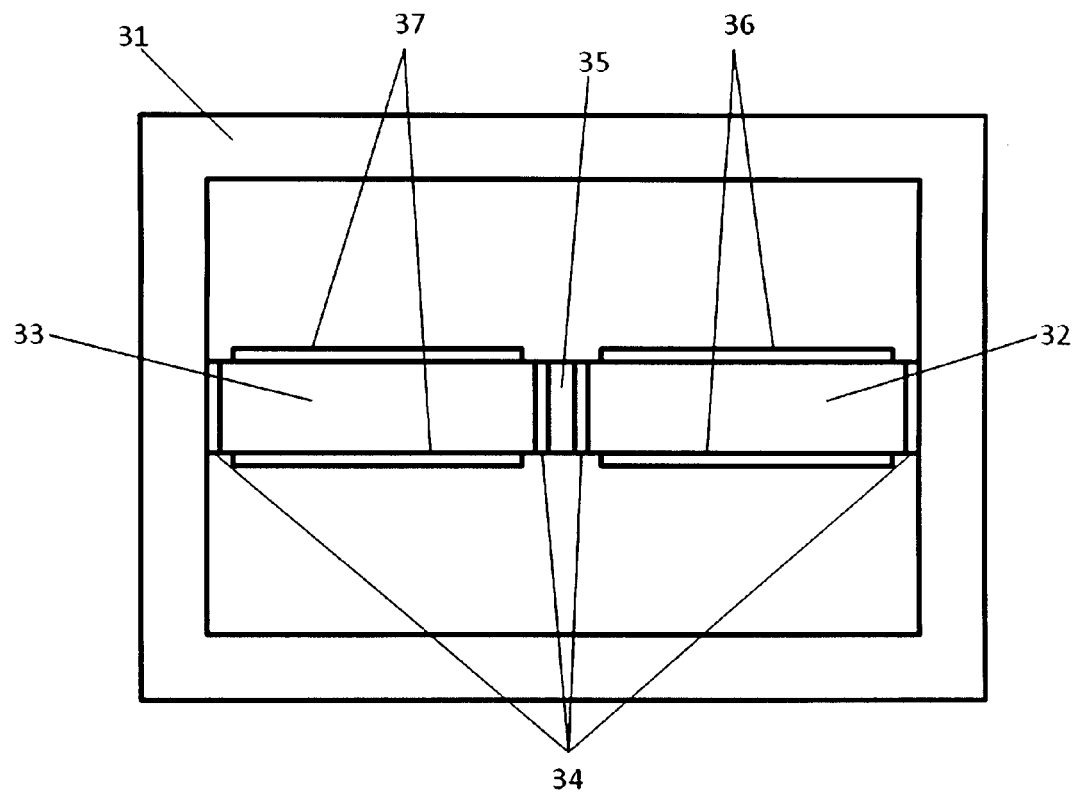
FIGS. 3 is a diagram of one embodiment of the mechanical properties testing device for micro specimens.

In another embodiment, the mechanical properties device is constructed for use in the measurement of mechanical properties of micro-size specimens as shown in FIG. 3. This micro machine facilitates measuring both strain and stress in the materials only by monitoring the input and output electrical signals. The machine consists of a first piezoelectric member 32 and a second piezoelectric member 33 fabricated on both sides of the specimen 35 and constrained in a frame 31. In this embodiment, the specimen 35 is a conductive metallic material and therefore, layers of nonconductive material 34 are fabricated on both ends of the first piezoelectric member 32 and both ends of the second piezoelectric member 33. These layers of nonconductive material 34 prevent the input electrical signal from disturbing the output electrical signal. The layers of non-conductive material 34 are rigid so that their deformation is negligible. These can be materials such as glass, quartz, alumina, or other appropriate materials. The layers of nonconductive material 34 may not be required if the piezoelectric members are made from non-conductive materials or if the specimen is nonconductive. Another configuration to reduce interactions between the input and output electric fields is to use piezoelectric materials with different chemical compositions for the first and second piezoelectric members or to change the crystal orientation of the two piezoelectric members with respect to each other. An input electrical signal is applied to the input conducting plates 36 adjacent to the first piezoelectric member 32. This induces some deformation in the first piezoelectric member 32 which exerts a force on the specimen 35. Since the specimen 35 is constrained on both sides, the specimen 35 is deformed and induces a force on the second piezoelectric member 33. This force causes the second piezoelectric member 33 to deform and thus produce an output electrical signal which is detected by the output conducting plates 37. Knowing the fundamental material constants of the piezoelectric materials, stresses and strains are calculated from the input and output electrical signals.

Figure 4A:
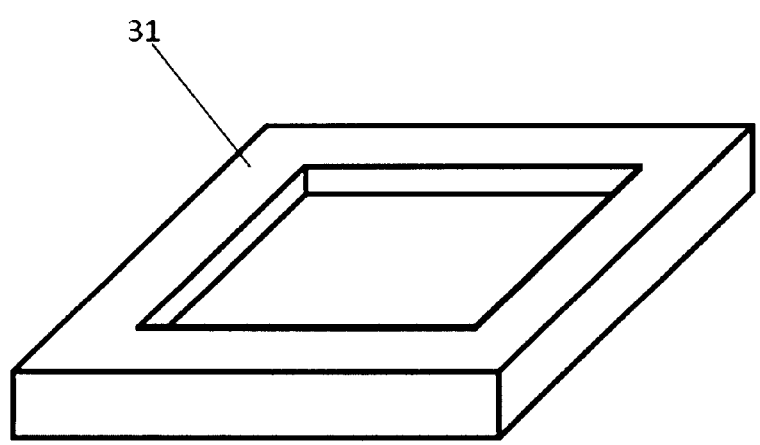
FIGS. 4a-h show the steps for preparing the mechanical properties testing device using MEMS processing technology.
Figure 4B:
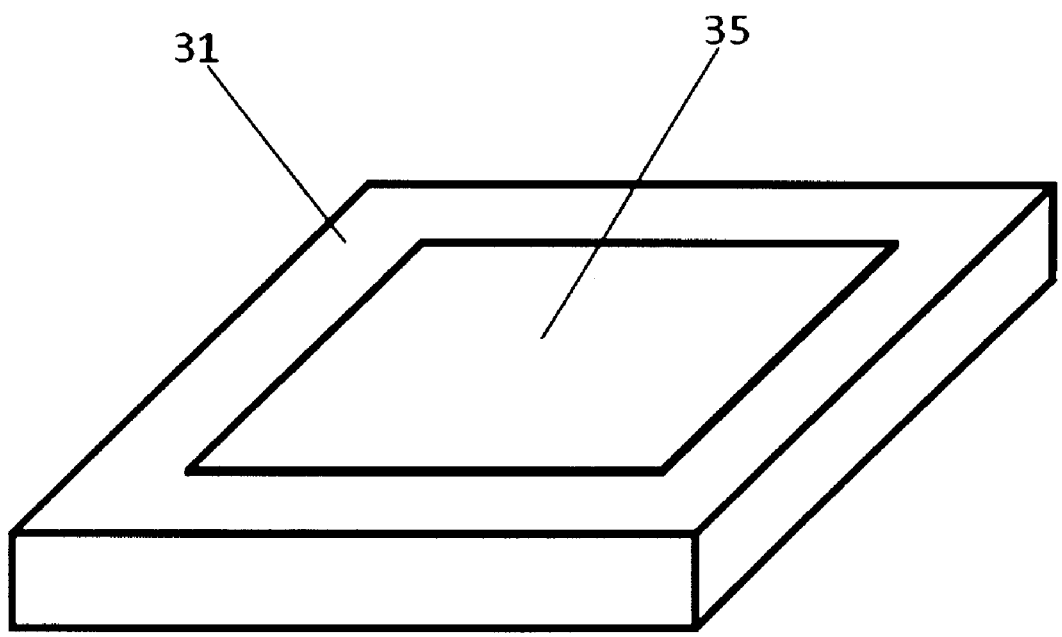
Figure 4C:
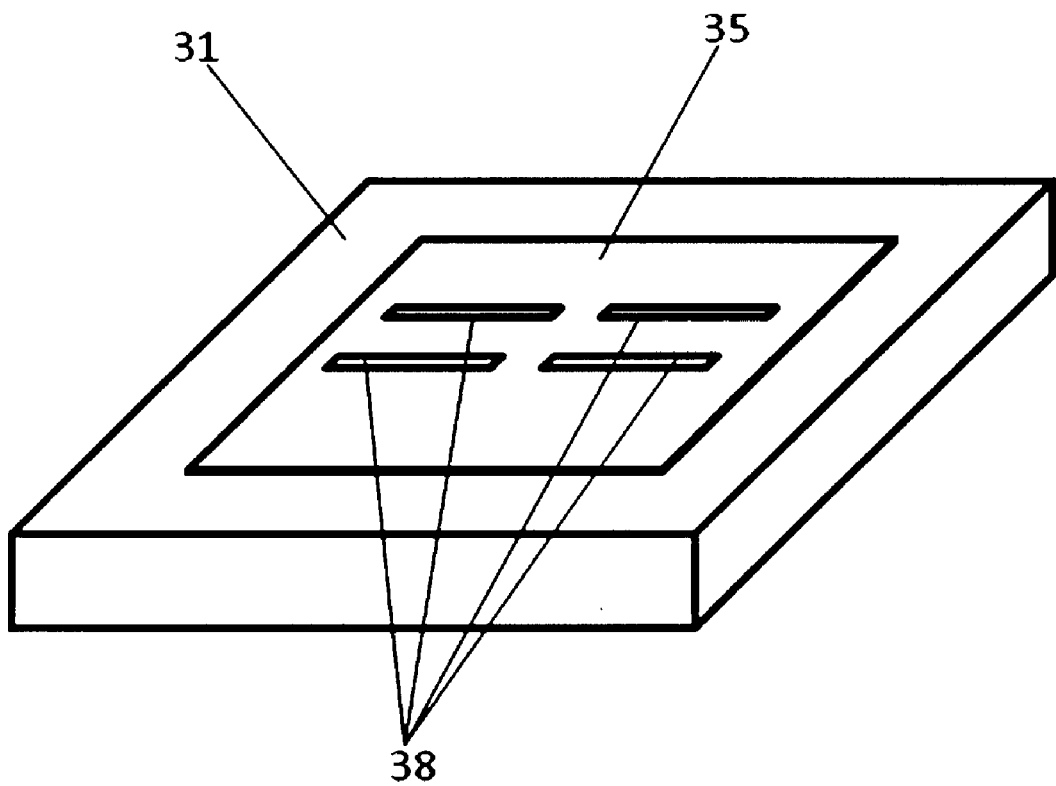
Figure 4D:
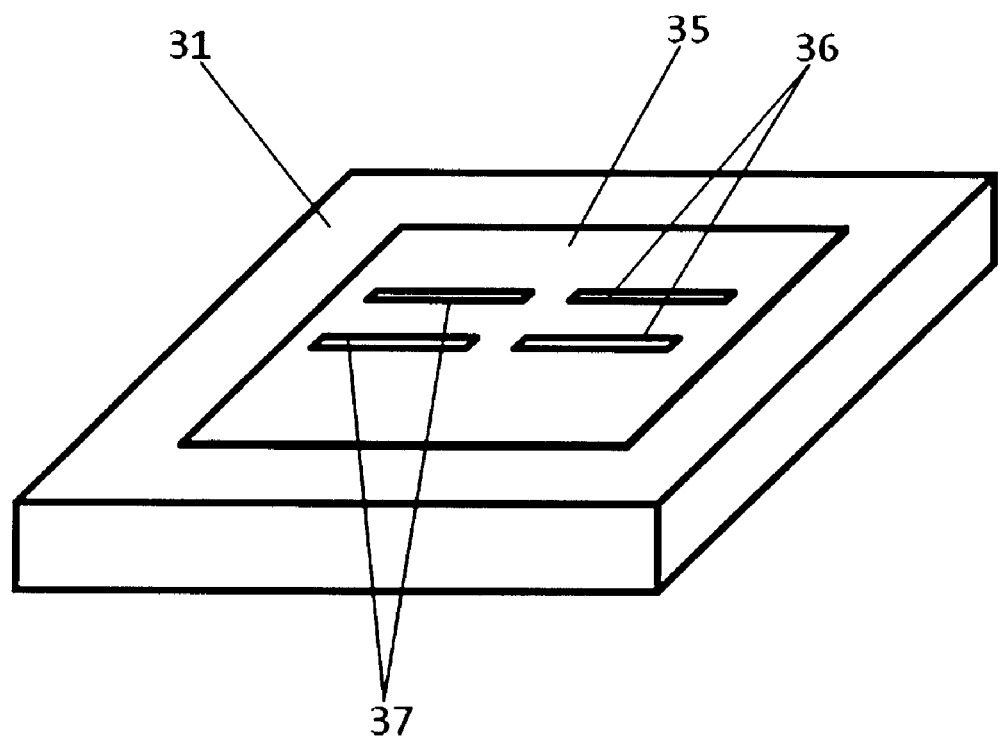
Figure 4E:
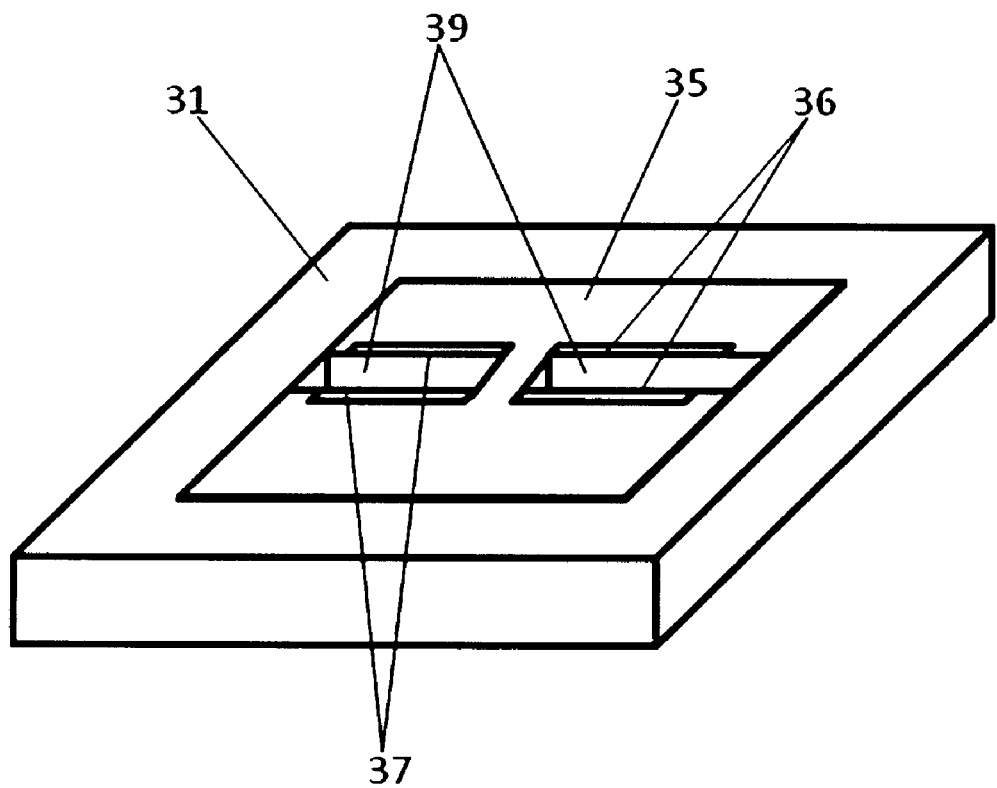
Figure 4F:
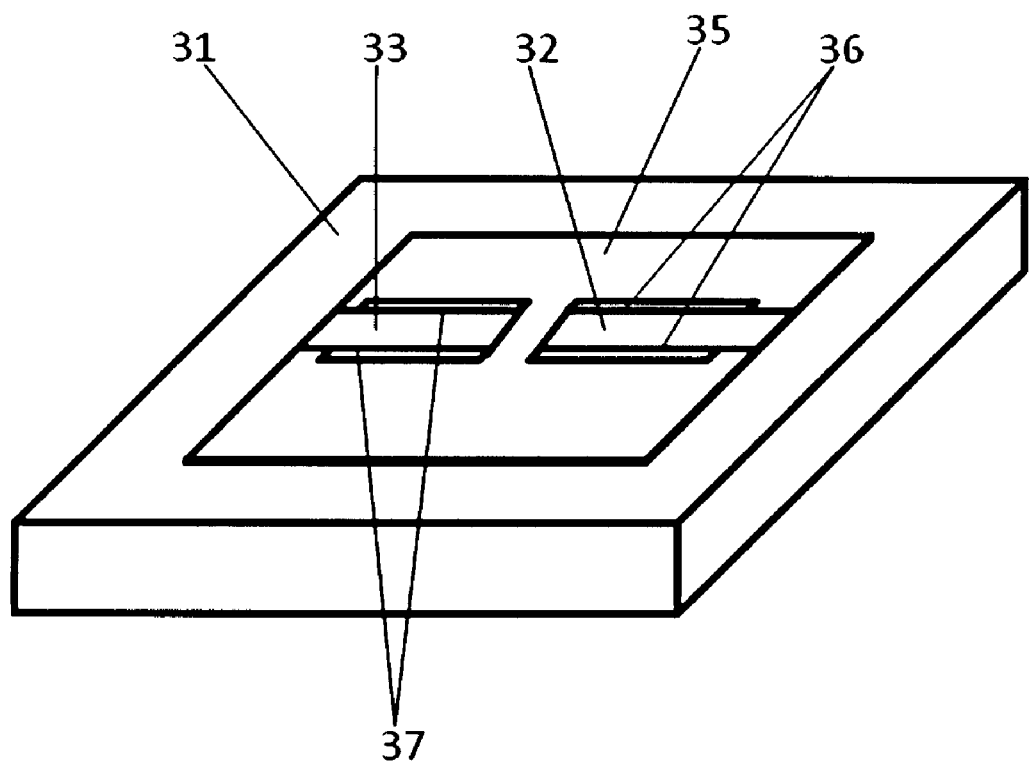
Figure 4G:
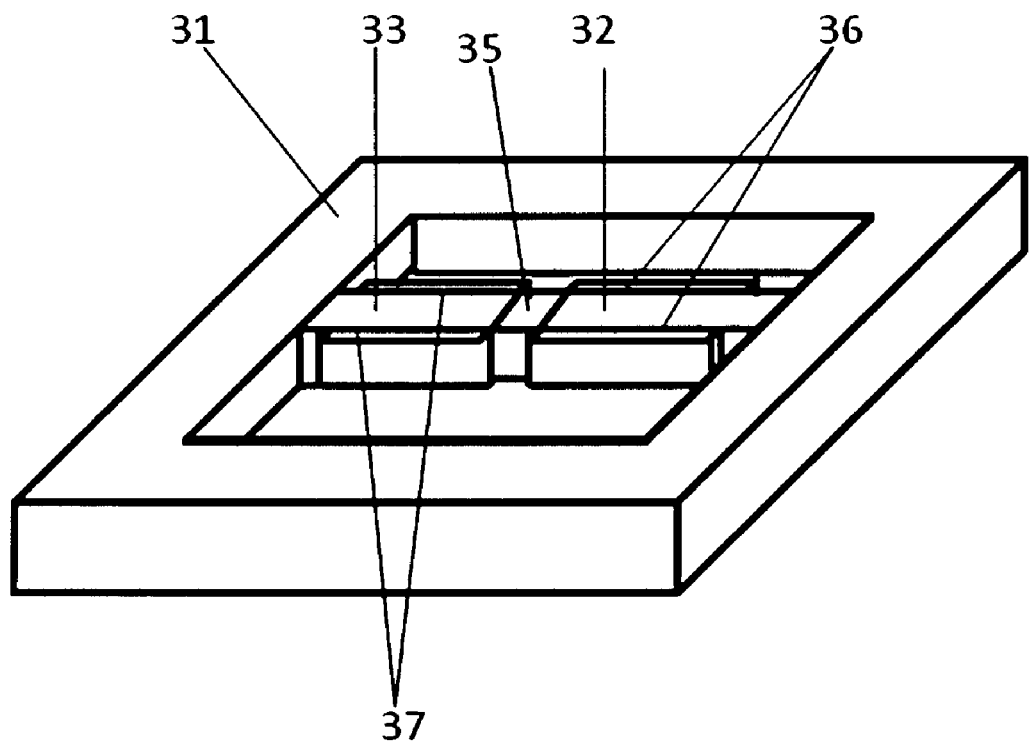
Figure 4H:
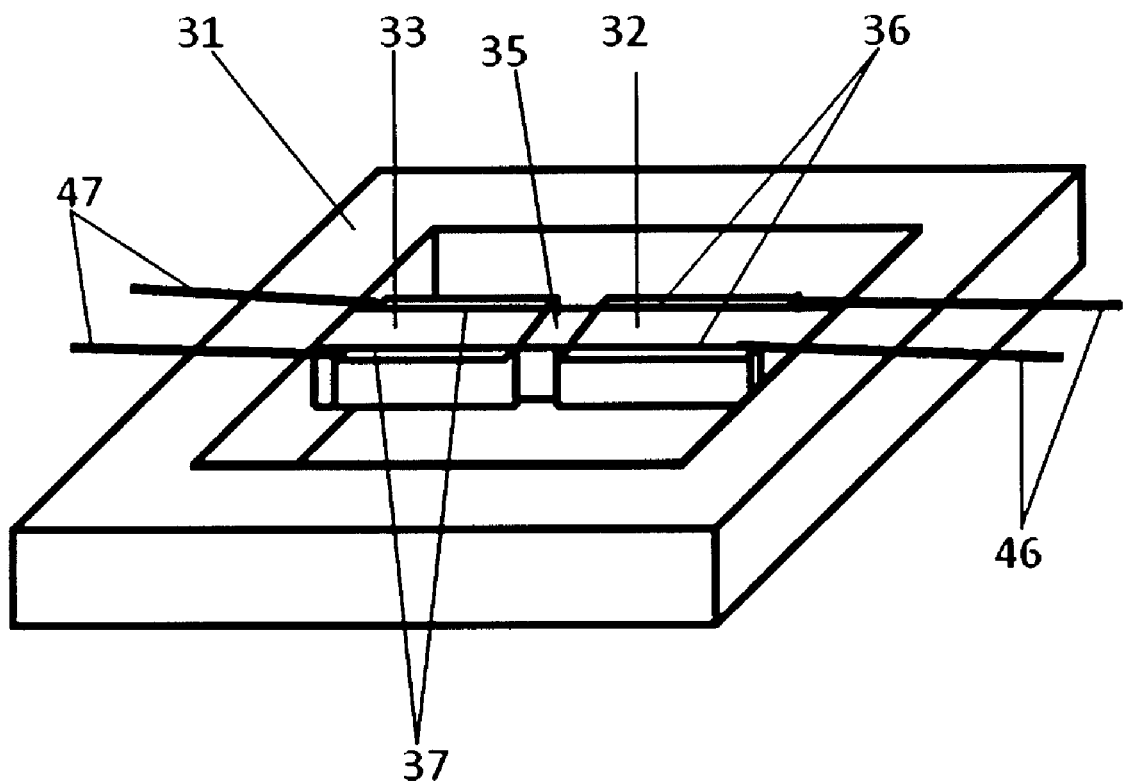

One method for preparing the specimen and test device for micro scale applications involves jointly fabricating the specimen and test device together. This is done in a clean room using micro fabrication methods. The steps for micro fabricating the specimen and test device specimen are shown in FIG. 4a-h. In the first step, FIG. 4a, a frame 31 is created by etching a cavity in silicon or any other appropriate type of substrate using a micro-fabrication technique such as photolithography, or micro-machining, or other appropriate technique. FIG. 4b shows the next step in which the specimen 35 (material to be tested) is deposited inside the frame 31. The deposition can be done using different techniques such as stencil printing, CVD or PVD, sputtering, or other appropriate technique. The type of deposition depends on the material type and the feasibility and ease of fabrication technique. A photolithography and etching process then follows to remove four strips 38 of material as shown in FIG. 4c. These four strips 38 go completely through the thickness of the material to be tested 35. The ends of these four strips 38 do not go completely to the frame 31. Referring to FIG. 4d, the four strips 38 are then filled with copper or any electrical conductive material to form the input conducting plates 36 and output conducting plates 37 by a deposition technique such as stencil printing, CVD or PVD, sputtering or other appropriate technique. The type of deposition depends on the material type and the feasibility and ease of fabrication technique. The input conducting plates 36 do not necessarily need to be the same material as the output conducting plates 37. The conducting plates can be positioned differently so the input electrical signal can be applied to induce deformation in different piezoelectric crystal orientations. FIG. 4e shows the next step in which two cavities 39 are formed by removing the material between the input conducting plates 36 and removing the material between the output conducting plates 37 by etching or other appropriate method to form. This material is removed all the way to the frame 31. Piezoelectric material is deposited in these cavities, as shown in FIG. 4f, by standard micro fabrication methods to form the first piezoelectric member 32 and the second piezoelectric member 33. The material removal or etched from the previous step is such that in the region where the piezoelectric material is in contact with the frame, the piezoelectric material is chamfered. This allows the piezoelectric members to deform freely without constraints. The first piezoelectric member 32 does not necessarily need to be the same chemical composition as the second piezoelectric member 33. The next step, shown in FIG. 4g, is the removal of the material between the conducting plates 36 and 37 and the frame 31 by standard micro fabrication methods. The specimen 35 remains as a thin film sandwiched between the first piezoelectric member 32 and the second piezoelectric member 33. FIG. 4h shows the final steps of securing an electrical connection 46 from the input electrical source to the input conducting plates 36 and an electrical connection 47 from the output conducting plates 37. The back of the frame is etched to create a free standing beam, constrained by a frame 31, with the specimen 35 sandwiched between the first piezoelectric member 32 and the second piezoelectric member 33.

It will be obvious to those having skill in the art that many modifications may be made to the details of the above described embodiments without departing from the underlying principles of the invention. For example, a micro scale fabrication method can involve securing the specimen between the piezoelectric members using epoxy, or other means of attachment, and then fabricating the frame and conducting plates. Other materials that change dimensions as a result of another type of applied field, such as magneto restrictive materials that change dimensions in the presence of magnetic fields, can be used in the disclosed invention.

What is claimed is:

1. A device for testing a specimen comprising:
   a system structure comprising a rigid frame,
   a first member, made from a material that changes dimensions in the presence of an applied field, supported by said structure, and
   a second member, made from a material that changes dimensions in the presence of an applied field, supported by said structure;
   wherein said rigid frame constrains one end of said first member and one end of said second member; and
   a position between said first member and said second member to place said specimen to be tested;
   an input field generator wherein said input field generator generates an input field around said first member;
   an output field detector wherein said output field detector measures an output field around said second member; and
   a processor communicatively coupled to said output filed generator; and said processor configured to calculate mechanical characteristics of said specimen.

2. The device of claim 1 wherein said specimen is secured between said first member and said second member such that both tensile and compressive forces and strains can be measured.

3. The device of claim 1 wherein said first member and said second member have a chamfered end in contact with said system structure.

4. The device of claim 1 wherein said first member is a first piezoelectric material and said second member is a second piezoelectric material.

5. The device of claim 4 wherein the crystallographic orientation of said first piezoelectric member is not the same as the crystallographic orientation of said second piezoelectric member.

6. The device of claim 4 wherein the chemical composition of said first piezoelectric member is not the same as the chemical composition of said second piezoelectric member.

7. The device of claim 4 wherein said input field and said output field are electric fields.

8. The device of claim 7 wherein:
   said input field generator includes two parallel conductive layers located such that said first piezoelectric member is between said conductive layers.

9. The device of claim 7 wherein:
   said output field detector includes two parallel conductive layers located such that said second piezoelectric member is between and in contact with said conductive layers.

10. The device of claim 7 further comprising:
    non-electrical conductive layers located between said first piezoelectric member and said specimen and between said specimen and said second piezoelectric member.

11. The device of claim 1 wherein said first member is a first magnetorestrictive material and said second member is a second magnetorestrictive material.

12. The device of claim 11 wherein the chemical composition of said first magnetorestrictive member is not the same as the chemical composition of said second magnetorestrictive member.

13. The device of claim 11 wherein said input field and said output field are magnetic fields.

14. The device of claim 13 wherein said input field generator is an electromagnet configured to generate said input magnetic field around said first magnetorestrictive member.

15. The device of claim 13 further comprising:
    non-magnetic layers located between said first magnetorestrictive member and said specimen and between said specimen and said second magnetorestrictive member.

16. The device of claim 1 wherein said first member is a magnetorestrictive material and said second member is a piezoelectric material.

17. The device of claim 16 wherein said input field is a magnetic field and said output field is an electric field.

18. The device of claim 16 wherein said input field generator is an electromagnet configured to generate said input magnetic field around said magnetorestrictive member.

19. The device of claim 16 wherein said output field detector comprises two parallel conductive layers, used to measure said output electric field located such that said piezoelectric member is between and in contact with said conductive layers.

20. A method for measuring deformation in a material comprising:
    (i) mounting a specimen to be measured between a first dimensional change member that changes dimensions in the presence of an applied field, and a second dimensional change member that changes dimensions in the presence of an applied field, wherein the first dimensional change member and second dimensional change member are constrained by a rigid frame that constrains one end of the first dimensional change member and one end of the second dimensional change member;
    (ii) applying an input field using an input field generator to said first member causing a change in dimension of said first member and transferring a force to said specimen which transfers a force to said second member causing said second member to deform resulting in the generation of an output field;
    (iii) measuring said output field using an output field generator; and
    (iv) using said output field and the fundamental material constants of said first member and second member to calculate the stress state in said specimen.

21. The method of claim 20 wherein said first dimensional change member is a piezoelectric material or magnetorestrictive material and said second dimensional change member is a piezoelectric material or magnetorestrictive material.

22. The methods of claim 20 wherein said input field is an electric field or a magnetic field and said output field is an electric field or a magnetic field.

23. A process for fabricating a Micro Electro Mechanical System fatigue testing apparatus, comprising:
 creating a frame in a substrate;
 depositing the material to be tested inside said frame;
 removing four strips of said material to be tested parallel to the longitudinal axis of said substrate, two strips collinear on each side of the center of said frame to a depth equal to the depth of said material, such that there are two sets of opposing parallel strips, with spaces between said collinear strips and between the end of said strips and said frame;
 filling said four strips with a conducting material to create two sets of opposing parallel conducting plates;
 removing the two regions of said material to be tested between said two sets of conducting plates and extending to said frame with the region adjacent to said frame indented to create two cavities, chamfered at said frame end and separated by a layer of said material to be tested;
 depositing a piezoelectric material in said two cavities;
 removing the remaining said material to be tested within said frame with the exception of the region between said piezoelectric material;
 attaching electrical contacts to said conducting material;
 removing the back surface of said frame.

24. The method of claim 20, wherein the specimen is a material chosen from a group consisting of conductive metallic materials, nonconductive metallic materials, thin films, micro-scale materials, macro-scale materials, polymers, and combinations thereof.

* * * * *